United States Patent
Duffy et al.

(10) Patent No.: US 6,197,592 B1
(45) Date of Patent: Mar. 6, 2001

(54) CLINICAL CONTROL MATERIALS FOR DETECTION OF BONE RESORPTIVE MARKERS

(75) Inventors: Thomas H. Duffy, Santa Ana; Hanh Onishi, Irvine, both of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/353,977

(22) Filed: Jul. 15, 1999

(51) Int. Cl.$^7$ ................................... G01N 31/00
(52) U.S. Cl. ................ 436/8; 436/174; 436/175; 436/177
(58) Field of Search .................. 436/8, 15, 17, 436/63, 174, 175, 177; 702/19

(56) References Cited

U.S. PATENT DOCUMENTS

| | | | |
|---|---|---|---|
| 5,350,855 | * 9/1994 | Daniloff et al. | 546/291 |
| 5,354,662 | * 10/1994 | Stone et al. | 435/7.92 |
| 5,589,346 | * 12/1996 | Kanan et al. | 435/7.92 |
| 5,700,693 | * 12/1997 | Robins | 436/64 |
| 5,744,096 | * 4/1998 | Jones et al. | 422/58 |

OTHER PUBLICATIONS

Pierre D. Delmas, et al., Biochemical Markers of Bone Turnover In Osteoporosis, *Rev. Rhum* [Engl. Ed.], 1997, 64 (6, suppl.), 31S–36S.

* cited by examiner

*Primary Examiner*—Maureen M. Wallenhorst
(74) *Attorney, Agent, or Firm*—Townsend and Townsend and Crew LLP

(57) ABSTRACT

Control materials containing specified concentrations of the osteoporosis markers deoxypyridinoline, pyridinoline, C-telopeptide and N-telopeptide in a matrix that is substantially the same as that of human urine are prepared by selecting amounts of human urine that contain sufficient quantities of the markers to achieve the target levels upon concentration, lyophilizing the selected urine, optionally after clarification by filtering, freezing and thawing, and pH adjustments, then reconstituting the lyophilized material, and combining and/or diluting the lyophilized material, either before or after reconstitution, to adjust the marker contents to the target levels. Surprisingly, the markers survive this process sufficiently intact to serve as reliable control materials of known composition and concentration.

24 Claims, No Drawings

CLINICAL CONTROL MATERIALS FOR DETECTION OF BONE RESORPTIVE MARKERS

BACKGROUND OF THE INVENTION

Osteoporosis, or bone loss, is a condition that accompanies aging as well as a variety of diseases of diverse etiology. These diseases include metabolic bone diseases, hypogonadism, hyperadrenocorticism, scurvy, heritable disorders of connective tissue such as osteogenesis imperfecta, homocystinuria, and Ehlers-Danlos syndrome, and other conditions such as rheumatoid arthritis and idiopathic osteoporosis. Age-related osteoporosis is particularly prevalent among post-menopausal women.

If detected early, osteoporosis can be treated by nutritional supplements, hormone replacement therapy, and certain prescription drugs. Unfortunately, osteoporosis is not readily identifiable by physical examination, and often remains undetected until a bone fracture occurs causing the individual to suffer pain, and possible deformity and disability. As one gets older, the ability to respond to these treatments diminishes, and the complications become more serious. Thus, early detection is an important means of lessening or preventing the consequences of osteoporosis, and improving the quality of life for those who are susceptible to this condition.

Osteoporosis is detectable by a variety of methods. These include x-ray absorptiometry by single-energy, dual-energy and peripheral means, radiographic absorptiometry, quantitative computed tomography, quantitative ultrasound, bone densitometry, and the chemical analysis of urine samples. The most convenient and cost-effective method is the chemical analysis of a urine sample to detect the levels of certain biochemical markers of bone turnover. The higher the rate of resorption relative to the rate of formation of bone tissue, the greater the rate of bone loss. The level of resorption in particular is readily determined on a quantitative basis by the analysis of urine for breakdown products of bone mineral and matrix. These breakdown products, or markers, are the collagen crosslinks pyridinoline and deoxypyridinoline, and the type I collagen breakdown products N-telopeptide and C-telopeptide.

Assays of urine for these markers is done by high-performance liquid chromatography (HPLC) and by immunoassays. These immunoassays can be performed on automated equipment for enhanced efficiency and to permit the analysis of large numbers of samples. As with any clinical analysis, quality control requires that precision and accuracy be maintained in the performance of the test and the analysis of the test results. For this reason, the use of control materials, which contain known amounts of the markers, is an important component of the laboratory protocol. Unfortunately, the isolation and purification of the markers from urine, either normal urine or urine having an elevated level of the markers, is a tedious and cumbersome process, and for this reason the controls for these markers are very expensive, and at times prohibitively so. A further disadvantage of controls prepared in this manner is that they are primarily buffer solutions in which the markers are dissolved, and buffer solutions differ substantially from the patient's urine sample. This affects the analytical procedures and detracts from the ability to make direct comparisons between the controls and the test samples.

SUMMARY OF THE INVENTION

It has now been discovered that liquid controls for determinations of the four biochemical markers of osteoporosis in urine can be made by using urine-based materials that have been purified primarily by lyophilization and reconstitution, without the use of chromatographic means to extract the markers and separate them from other species present in urine. The urine-based materials may be derived either from normal urine or from urine with elevated levels of the markers. Lyophilization and reconstitution, together with the removal of extraneous substances that precipitate and do not redissolve, produce a clarified quantity of urine and, surprisingly, do so without loss or destruction of the markers present in the urine. The amount of each marker present in the starting urine is thus retained through the processing. Reconstitution with water produces a control solution whose matrix is clear yet highly similar to the patient's sample urine. The marker concentration can be controlled by the proportion of water used for reconstitution, and two or more aliquots can be combined to achieve any particular combination of the markers at target concentrations. The invention thus provides controls that are sufficiently clear to be suitable for use, that are sufficiently stable to be clinically useful, and that contain the markers in precisely known concentrations, and yet are inexpensive and easy to prepare while offering the added advantage of a matrix that is highly similar to those of the test samples. These qualities enable the control materials of this invention to facilitate reliable and accurate quantitation of samples of urine.

These and other features, objects, and advantages of the invention will be more readily understandable from the description that follows.

DESCRIPTION OF THE SPECIFIC EMBODIMENTS

This invention is directed to control materials for bone resorption marker determinations in urine samples and methods for their preparation of such control materials. The invention extends to control materials that contain only one of the four markers—pyridinoline, deoxypyridinoline, N-telopeptide, and C-telopeptide—and it also extends to control materials that contain two or more of these markers in combination, including control materials that contain all four. The choice of marker(s) for a particular control material will be governed by the marker whose presence is to be determined and quantified. The choice of marker(s) will vary with the preference or intentions of the manufacturer of the assay with which the control material(s) are to be used, the assay protocol itself, and the preference of the individual user. The materials of this invention may be used as controls, as well as calibrators and standards that contain the designated markers in known concentrations.

The terms "N-telopeptide" and "C-telopeptide" are used herein in the manner in which they are used by biochemists, to refer to sequences of about 12 to 25 amino acids that occur at the N- and C-terminals of the tropocollagen molecule. The terms "N-telopeptide" and "C-telopeptide" each refer to a class of species and each generally includes a mixture of species, including crosslinked species, within the class rather than a single species. Nevertheless, the presence and significance of N-telopeptide and C-telopeptide in urine for diagnoses of osteoporosis, as well as the meanings of the terms, are well recognized in the medical community. In this specification, C-telopeptide is represented by the abbreviation "CTX" and N-telopeptide by the abbreviation "NTX." Due to its heterogeneity, NTX is expressed in terms of "bone collagen equivalents" ("BCE"), a term that is likewise recognized among practitioners who diagnose and treat osteoporosis. To compensate for the variations in urine concentrations that normally occur in a donor over the span of a typical day, the measured levels of CTX and NTX are normalized with respect to creatinine. Creatinine is selected for this purpose since it is expelled into the urine at a substantially constant rate. Its concentration in urine is thus a direct indication of the normal variations in urine concentrations occurring over the course of a day, and is therefore an appropriate normalizing factor. The CTX and NTX levels are thus expressed as $\mu$g/L per mM creatinine and nM BCE per mM creatinine, respectively.

The terms "peptide-free pyridinoline" and "peptide-free deoxypyridinoline" refer to proteolytically decomposed species, while "pyridinoline" and "deoxypyridinoline" each refer to a mixture of species which may retain attached protein. HPLC assays tend to read total pyridinoline and total deoxypyridinoline while immunoassays tend to read total pyridinoline and total deoxypyridinoline up to a certain maximum fragment length, typically 1,000 kilodaltons or less. While assay procedures are known that distinguish between pyridinoline and deoxypyridinoline, certain assay procedures do not distinguish between them, providing instead a value for the combined concentrations or amounts of these two markers. This invention likewise extends to control materials for assays where these two markers are identified collectively or individually. In this specification, pyridinoline will be represented by the abbreviation "PYD," deoxypyridinoline by the abbreviation "DPD," and combinations of the two by the abbreviation "PYD/DPD."

The initial stage in the preparation of the control materials of this invention is the selection of urine specimens as sources for the materials. The specimens are selected on the basis of their amounts of the markers to be included in the control materials ultimately formed. Thus, for a PYD control material, the starting urine specimen will be one that contains high amounts of PYD, and likewise for the other three markers. Two or more such specimens may be required to obtain the needed total amount of the marker, or to limit the specimen volume if such a limitation is required by the processing equipment (such as the vacuum dryer used for lyophilization). Similarly, when preparing a single control material for two or more markers, the starting urine specimens will be either one specimen containing all of the designated markers in high amounts or two or more specimens that collectively contain all of the designated markers in high amounts.

The amount of marker present in the starting urine specimen is not critical to the invention and may vary widely. For convenience and efficiency, specimens with relatively high concentrations of the markers are preferred. Thus, for a DPD control material, the starting specimen is preferably one that contains DPD at a concentration of at least about 20 nM. Similarly, for a PYD/DPD control material, the starting specimen is preferably one that contains PYD and DPD in a combined concentration of at least about 100 nM. Likewise, for an NTX control material, the starting specimen is preferably one that contains NTX at a concentration of at least about 50 nM BCE per mM creatinine. Finally, for a CTX control material, the starting specimen is preferably one that contains CTX at a concentration of at least about 200 $\mu$g/L per mM creatinine.

The urine that is used as the starting specimen to serve as the source for the markers is human urine, either from male donors or female donors, including pregnant female donors and donors with elevated levels of bone resorptive markers. In preferred methods of practicing the invention, the specimen or pooled specimens are first filtered to remove solid matter and to improve clarity by reducing turbidity. Turbidity may be further reduced by adjusting the pH to a value of between about 4.0 and about 5.0, preferably about 4.5, then freezing and thawing the urine. This is preferably followed by filtration, using a filter of at least about 0.8 micron retention. The term "0.8 micron retention" is used in this context to indicate that particles of 0.8 micron and greater will be retained by the filter. The term "at least" is used to indicate that filters of smaller size openings may be used as well. The pH is then preferably raised to a basic level such as one within the range of about 7.8 to about 8.5, preferably about 8.0, and then optionally frozen once again for storage. These various pH adjustments, freeze-thaw cycles, and filtrations serve to stabilize the specimens for until they are ready for use and to precipitate out some of the proteins and clarify the specimens, thereby facilitating the analyses that will follow for determination of the levels of DPD, PYD, CTX, and NTX present in the specimens.

Analyses are then conducted by conventional means, prominent among which are immunometric techniques. Immunometric analysis kits are commercially available for each of the four markers addressed in this invention. A DPD kit for example is available from Bayer Corporation, Walpole, Mass., U.S.A.; a PYD/DPD kit is available from Metra Biosystems, Mountain View, Calif., U.S.A.; an NTX kit is available from Ostex, Seattle, Wash., U.S.A., and a CTX kit is available from DSL, Webster, Tex., U.S.A.

Once the specimens are analyzed, specimens with relatively high amounts of the markers are selected for the lyophilization to follow. The selection criteria are not critical to this invention, but in general the higher the amounts of one or more of the markers in the specimens, the more useful they will be as sources for the control materials ultimately made. A typical set of selection criteria, offered here as an example, is DPD greater than 20 nM, PYD/DPD greater than 100 nM, NTX greater than 50 nM BCE per mM creatinine, and CTX greater than 200 $\mu$g/L per mM creatinine. These amounts may either be in individual specimens or two or more may be present together in a common specimen.

Once the specimens are selected, and optionally pooled to achieve volumes large enough for efficient processing, the specimens are lyophilized. Conventional lyophilization procedures and equipment may be used. In general, the procedure involves lowering the temperature of a specimen to a level below the eutectic point of the specimen, then lowering the pressure sufficiently to remove water from the specimen by sublimation. Some of the suppliers for lyophilization equipment are FTS Systems, Life Science Division, Stone Ridge, N.Y., U.S.A.; Formatech, Inc., Lowell, Mass., U.S.A.; and Hull Corporation, Hatboro, Pa., U.S.A.

Once lyophilized, the materials are reconstituted by the addition of distilled or otherwise purified water, at proportions calculated to achieve desired concentrations for use as the control materials. The final concentrations are not critical, and may vary according to the wishes of the manufacturer, supplier, distributor or user. As mentioned above, a single control may contain one, two three or all four of the markers at specified concentrations. In many cases, it will be useful to prepare a series of control materials at different concentrations of the markers, spanning or bracketing the range of concentrations that might be expected in the samples or that might be indicative of the presence of a disease state that is associated with a high level of bone resorption. For example, a series of control materials may include one control material in which the concentration of the marker(s) is approximately equal to that of a patient not suffering from osteoporosis, a second control material containing the marker(s) at a concentration substantially higher than (e.g., approximately twice) that of the first control material, and a third control material containing the marker(s) at a concentration substantially higher than those of both the first and second control materials (e.g., approximately three times that of the first control material). Other combinations and concentrations will be readily apparent to those skilled in the art.

Once the materials are reconstituted in the desired combinations and concentrations, it is often desirable to lyophilize the materials once again, optionally after filtering them once again, to supply to the distributor or user in lyophilized form. The final lyophilized materials will then be supplied with instructions for reconstituting them. The filtration prior to the final lyophilization may be at the same retention size or at a finer retention size for further purification.

The following examples are offered solely for purposes of illustration.

EXAMPLE 1

Human Urine Collection

Raw human urine specimens are pooled to achieve volumes of approximately 50 liters per pool, and filtered through pads of at least 0.8 micron retention. The pH of each pool is adjusted to 4.5±0.1 with concentrated HCl. The pools are frozen, thawed, and then filtered through pads of at least 0.8 micron retention. The pH of each pool is adjusted to 8.0±0.1 using 6N NaOH. The pools are then stored frozen at −20° C.

EXAMPLE 2

Assay of Human Urine Pools

The frozen urine pools from Example 1 are thawed and assayed for the presence of DPD, PYD/DPD, CTX, and NTX by immunometric techniques performed with kits available from commercial suppliers. Pools with the following criteria are selected for lyophilization: DPD greater than 20 nM, PYD/DPD greater than 100 nM, NTX greater than 50 nM BCE per mM creatinine, CTX greater than 200 µg/L per mM creatinine, or any combination thereof.

EXAMPLE 3

Lyophilization

The selected pools are placed in lyophilization pans, each pan having a fill volume of 1.5 L. Lyophilization is then conducted in an industrial vacuum dryer, Hull Corporation Model 651VC36F40). The procedure consists of lowering the shelf temperature to −29° C. or below prior to loading the pans, then loading the pans and cooling the contents to the lowered shelf temperature, then imposing a vacuum by lowering the pressure to below 10 mmHg. This is followed by raising the shelf temperature to −7° C. and maintaining it at this level until all of the pools reach −18° C. The shelf temperature is then increased to +5° C. and maintained at this level until all pools reach −1° C. The shelf temperature is then raised to +16° C., where it is maintained until all pools reach +10° C. The temperature is then increased to +27° C. where it is maintained until all pools reach +21° C. The temperature is then increased to +43° C. where it is maintained until all pools reach +38° C. The pools are held at this temperature for twelve hours. The dryers are then vented to raise the pressure to atmospheric pressure, and the lyophilized material is removed from the pans.

EXAMPLE 4

Reconstitution

Lyophilized materials from Example 3 are reconstituted by dissolving them in distilled water to achieve a total volume that is one-tenth the original volume and hence a concentration that is ten times that of the original pools. The reconstituted materials are pooled and filtered through a 0.45-micron filter cartridge, and assayed for DPD, PYD/DPD, NTX, and CTX as in Example 2. The materials are then diluted to the desired target concentrations with distilled water, filtered through a 0.45-micron filter, placed in vials at 5.2 mL per vial, and lyophilized again. Prior to use, the user reconstitutes the lyophilized material to achieve a clear solution at the desired concentrations.

EXAMPLE 5

Marker Assays

Urine specimens were pooled, treated, lyophilized and reconstituted as described in Examples 1 through 4, and the total amounts of each of the four markers were determined both in the original specimens and in the materials after lyophilization and reconstitution. The quantities of the four markers both before (the original specimens) and after are listed below. The values in the "After" column are normalized back to the dilution of the original specimens to provide a direct comparison.

| Concentrations of Markers Before and After Processing | | |
|---|---|---|
| Marker | Before (original specimens) | After lyophilization and reconstitution |
| DPD (nM) | 24.8 | 28.2 |
| PYD/DPD (nM) | 585 | 597 |
| NTX (nM BCE/mM creatinine) | 192 | 263 |
| CTX (µg/L/mM creatinine) | 198.5 | 198.1 |

The foregoing is offered primarily for purposes of illustration. Further modifications and variations of the procedures and materials that are still within the scope of the invention will be readily apparent to those skilled in the art.

What is claimed is:

1. A control material for the detection of a bone resorption marker selected from the group consisting of deoxypyridinoline, pyridinoline, C-telopeptide and N-telopeptide in human urine, said control material prepared by a process comprising:

(a) selecting an aliquot of human urine that contains a detectable amount of said bone resorption marker;

(b) adjusting the pH of said aliquot to a value within the range of about 7.8 to about 8.5; and (c) lyophilizing said selected aliquot and reconstituting said aliquot thus lyophilized by dissolving in water to form a clear solution containing substantially the same amount of said bone resorption marker as said aliquot of human urine.

2. A control material in accordance with claim 1 in which said process further comprises clarifying said aliquot prior to step (c).

3. A control material in accordance with claim 1 in which said process further comprises adjusting the pH of said aliquot to an acidic pH value within the range of about 4.0 to about 5.0, freezing said aliquot at said acidic pH value, thawing said aliquot thus frozen, and filtering through pads of at least about 0.8 micron retention, all prior to step (b).

4. A control material in accordance with claim 1 in which said aliquot of human urine of step (a) contains deoxypyridinoline at a concentration of greater than 20 nM.

5. A control material in accordance with claim 1 in which said aliquot of human urine of step (a) contains pyridinoline and deoxypyridinoline at a combined concentration of greater than 100 nM.

6. A control material in accordance with claim 1 in which said aliquot of human urine of step (a) contains N-telopeptide at a concentration of greater than 50 nM of bone collagen equivalents per mM of creatinine.

7. A control material in accordance with claim 1 in which said aliquot of human urine of step (a) contains C-telopeptide at a concentration of greater than 200 μg/L per mM of creatinine.

8. A control material in accordance with claim 1 in which said process further comprises:
   (d) lyophilizing said reconstituted aliquot to place said control material in lyophilized form.

9. A control material in accordance with claim 1 in which said process further comprises:
   (d) filtering said reconstituted aliquot and lyophilizing said reconstituted and filtered aliquot to place said control material in lyophilized form.

10. A plurality of control materials in accordance with claim 1, the concentration of said bone resorption marker in a first control material of said plurality of control materials being approximately equal that of a patient not suffering from osteoporosis, and the concentration of said bone resorption marker in a second control material of said plurality of control materials being substantially higher than that of said first control material.

11. A plurality of control materials in accordance with claim 1, the concentration of said bone resorption marker in a first control material of said plurality of control materials being approximately equal that of a patient not suffering from osteoporosis, the concentration of said bone resorption marker in a second control material of said plurality of control materials being substantially higher than that of said first control material, and the concentration of said bone resorption marker in a third control material of said plurality of control materials being substantially higher than that of both said first and second control materials.

12. A control material for the detection of two or more bone resorption markers selected from the group consisting of deoxypyridinoline, pyridinoline, C-telopeptide and N-telopeptide in human urine, said control material prepared by a process comprising:
   (a) selecting one or more aliquots of human urine that collectively contain two or more of said bone resorption markers and pooling said aliquots; and
   (b) lyophilizing and reconstituting said aliquots by dissolving in water to form said control material as a single clear aqueous solution containing substantially the same amounts of said bone resorption markers as said aliguots of human urine.

13. A control material for the detection of the bone resorption markers deoxypyridinoline, pyridinoline, C-telopeptide and N-telopeptide in human urine, said control material prepared by a process comprising:
   (a) selecting one or more aliquots of human urine that collectively contain all four of said bone resorption markers and pooling said aliquots; and
   (b) lyophilizing and reconstituting said aliquots by dissolving in water to form said control material as a single clear aqueous solution containing substantially the same amounts of said bone resorption markers as said aliquots of human urine.

14. A control material in accordance with claim 13 in which said aliquots thus selected collectively contain deoxypyridinoline at a concentration of greater than 20 nM, pyridinoline and deoxypyridinoline at a combined concentration of greater than 100 nM, N-telopeptide at a concentration of greater than 50 nM of bone collagen equivalents per mM of creatinine, and C-telopeptide at a concentration of greater than 200 μg/L per mM of creatinine.

15. A process for the preparation of a control material for the detection of a bone resorption marker selected from the group consisting of deoxypyridinoline, pyridinoline, C-telopeptide and N-telopeptide in human urine, said process comprising:
   (a) selecting an aliquot of whole human urine that contains a detectable amount of said bone resorption marker;
   (b) adjusting the pH of said aliquot to a value within the range of about 7.8 to about 8.5; and
   (c) lyophilizing said selected aliquot and reconstituting said aliquot thus lyophilized by dissolving in water to form a clear solution containing substantially the same amount of said bone resorption marker as said aliquot of whole human urine.

16. A process in accordance with claim 15 further comprising clarifying said aliquot prior to step (c).

17. A process in accordance with claim 15 further comprising adjusting the pH of said aliquot to an acidic pH value within the range of about 4.0 to about 5.0, freezing said aliquot at said acidic pH value, thawing said aliquot thus frozen, and filtering through pads of at least about 0.8 micron retention, all prior to step (b).

18. A process in accordance with claim 15 in which said aliquot of whole human urine of step (a) contains deoxypyridinoline at a concentration of greater than 20 nM.

19. A process in accordance with claim 15 in which said aliquot of whole human urine of step (a) contains pyridinoline and deoxypyridinoline at a combined concentration of greater than 100 nM.

20. A process in accordance with claim 15 in which said aliquot of whole human urine of step (a) contains N-telopeptide at a concentration of greater than 50 nM of bone collagen equivalents per mM creatinine.

21. A process in accordance with claim 15 in which said aliquot of whole human urine of step (a) contains C-telopeptide at a concentration of greater than 200 μg/L per mM creatinine.

22. A process for the preparation of a control material for the detection of two or more bone resorption markers selected from the group consisting of deoxypyridinoline, pyridinoline, C-telopeptide and N-telopeptide in human urine, said process comprising:
   (a) selecting one or more aliquots of human urine that collectively contain two or more of said bone resorption markers and pooling said aliquots; and
   (b) lyophilizing and reconstituting said aliquots by dissolving in water to form said control material as a single clear aqueous solution containing substantially the same amounts of said bone resorption markers as said aliquots of human urine.

23. A process for the preparation of a control material for the detection of the bone resorption markers deoxypyridinoline, pyridinoline, C-telopeptide and N-telopeptide in human urine, said process comprising:

(a) selecting one or more aliquots of human urine that collectively contain all four of said bone resorption markers and pooling said aliquots; and (b) lyophilizing and reconstituting said aliquots by dissolving in water to form said control material as a single clear aqueous solution containing substantially the same amounts of said bone resorption markers as said aliquots of human urine.

24. A process in accordance with claim 23 in which said aliquots thus selected collectively contain deoxypyridinoline at a concentration of greater than 20 nM, pyridinoline and deoxypyridinoline at a combined concentration of greater than 100 nM, N-telopeptide at a concentration of greater than 50 nM of bone collagen equivalents per mM creatinine, and C-telopeptide at a concentration of greater than 200 µg/L per mM creatinine.

* * * * *